US012653482B2

(12) United States Patent
Takenaka

(10) Patent No.: US 12,653,482 B2
(45) Date of Patent: Jun. 16, 2026

(54) RADIATION IMAGING SYSTEM COMPRISING A RADIATION IMAGING APPARATUS INCLUDING A BURN-IN ESTIMATING UNIT

(71) Applicant: CANON KABUSHIKI KAISHA, Tokyo (JP)

(72) Inventor: Katsuro Takenaka, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 237 days.

(21) Appl. No.: 18/508,946

(22) Filed: Nov. 14, 2023

(65) Prior Publication Data

US 2024/0168180 A1     May 23, 2024

(30) Foreign Application Priority Data

Nov. 22, 2022    (JP) ................................ 2022-186150

(51) Int. Cl.
| | |
|---|---|
| *A61B 6/42* | (2024.01) |
| *A61B 6/00* | (2006.01) |
| *A61B 6/40* | (2024.01) |
| *G01N 23/04* | (2018.01) |
| *G01N 23/083* | (2018.01) |
(Continued)

(52) U.S. Cl.
CPC ............ *A61B 6/542* (2013.01); *A61B 6/4085* (2013.01); *A61B 6/4233* (2013.01); *A61B 6/545* (2013.01); *G01N 23/04* (2013.01); *G01N 23/083* (2013.01); *G01N 23/087* (2013.01); *G01N 23/18* (2013.01);
(Continued)

(58) Field of Classification Search
CPC ....... A61B 6/40; A61B 6/4085; A61B 6/4233; A61B 6/4258; A61B 6/4266; A61B 6/4283; A61B 6/486; A61B 6/487; A61B 6/488; A61B 6/52; A61B 6/5205; A61B 6/54; A61B 6/542; A61B 6/42; A61B 6/545; G01N 23/04; G01N 23/043; G01N 23/083; G01N 23/087; G01N 23/10; G01N 23/18; G01T 1/20; G01T 1/2006; G01T 1/2018; G01T 1/20182; G01T 1/20184; G01T 1/20188
USPC ............ 378/51, 53, 54, 56–58, 62, 63, 98.8; 250/370.09
See application file for complete search history.

(56) References Cited

U.S. PATENT DOCUMENTS

| | | | |
|---|---|---|---|
| 7,881,555 B2 * | 2/2011 | Spahn | ........................ G06T 5/40 345/20 |
| 8,903,048 B2 * | 12/2014 | Kitano | ................. A61B 6/4233 378/115 |

(Continued)

FOREIGN PATENT DOCUMENTS

JP      2003185752 A     7/2003

OTHER PUBLICATIONS

An English translation of JP2003185752A by Patent Translate (Year: 2003).*

*Primary Examiner* — Allen C. Ho
(74) *Attorney, Agent, or Firm* — Canon U.S.A., Inc. IP Division

(57) ABSTRACT

A radiation imaging apparatus includes a radiation detecting panel configured to convert radiation into an image signal, and a burn-in estimating unit configured to estimate, from the image signal, burn-in of the radiation detecting panel due to the radiation. When the burn-in estimating unit estimates that burn-in occurs, the burn-in estimating unit outputs information regarding stop of emission of the radiation to an external apparatus.

10 Claims, 10 Drawing Sheets

(51) Int. Cl.
    *G01N 23/087*       (2018.01)
    *G01N 23/18*         (2018.01)
    *G01T 1/175*         (2006.01)
    *G01T 1/20*          (2006.01)

(52) U.S. Cl.
    CPC ............... *G01T 1/175* (2013.01); *G01T 1/20*
    (2013.01); *G01T 1/20184* (2020.05)

(56)        References Cited

U.S. PATENT DOCUMENTS

| | | | |
|---|---|---|---|
| 9,372,268 B2 * | 6/2016 | Kondo | G01T 1/20 |
| 9,462,989 B2 * | 10/2016 | Takenaka | A61B 6/42 |
| 9,569,829 B2 * | 2/2017 | Ohguri | A61B 6/00 |
| 9,980,690 B2 * | 5/2018 | Muroi | A61B 6/52 |
| 10,074,679 B2 * | 9/2018 | Tajima | A61B 6/542 |
| 10,285,661 B2 * | 5/2019 | Morf | A61B 6/469 |
| 10,349,914 B2 * | 7/2019 | Takenaka | A61B 6/4233 |
| 10,537,295 B2 * | 1/2020 | Watanabe | A61B 6/4233 |
| 11,047,994 B2 * | 6/2021 | Terui | G01T 1/17 |
| 11,047,995 B2 * | 6/2021 | Yagi | G01T 1/208 |
| 11,067,706 B2 * | 7/2021 | Furumoto | A61B 6/542 |
| 11,073,626 B2 * | 7/2021 | Oike | G01T 1/2023 |
| 11,090,018 B2 * | 8/2021 | Watanabe | A61B 6/54 |
| 11,125,702 B2 * | 9/2021 | Hayashida | G01N 23/046 |
| 11,154,261 B2 * | 10/2021 | Okada | A61B 6/542 |
| 11,166,693 B2 * | 11/2021 | Saigusa | A61B 6/4208 |
| 11,241,210 B2 * | 2/2022 | Asai | A61B 6/563 |
| 11,246,554 B2 * | 2/2022 | Wang | A61B 6/544 |
| 11,272,899 B2 * | 3/2022 | Matsuda | A61B 6/545 |
| 11,360,034 B2 * | 6/2022 | Torii | A61B 6/4233 |
| 11,369,332 B2 * | 6/2022 | Kunieda | A61B 6/542 |
| 11,693,131 B2 * | 7/2023 | Kawanabe | G01T 1/2008 250/370.09 |
| 11,839,013 B2 * | 12/2023 | Niwa | A61B 6/585 |
| 11,957,499 B2 * | 4/2024 | Yin | A61B 6/4441 |
| 12,274,570 B2 * | 4/2025 | Tamura | A61B 6/4208 |
| 12,274,571 B2 * | 4/2025 | Hayashida | A61B 6/542 |
| 12,303,317 B2 * | 5/2025 | Umekawa | A61B 6/4291 |
| 12,329,554 B2 * | 6/2025 | Miura | A61B 6/4233 |

* cited by examiner

FIG. 4

RADIATION IMAGING SYSTEM COMPRISING A RADIATION IMAGING APPARATUS INCLUDING A BURN-IN ESTIMATING UNIT

BACKGROUND

Field of the Disclosure

The present disclosure relates to a radiation imaging apparatus and a radiation imaging system that acquire, as an image, an intensity distribution of radiation transmitted through an object.

Description of the Related Art

As an image capturing apparatus that is used for medical image diagnosis with an X-ray or for non-destructive inspection, a radiation imaging apparatus that uses a radiation detecting panel (flat panel detector (abbreviated as an FPD)) formed of a semiconductor material is widely used.

Such a radiation imaging apparatus can be used to inspect an internal flaw, a surface flaw, or deterioration of components such as a print board and piping without damaging the components in non-destructive inspection.

However, it is necessary to irradiate a scintillator with a large amount of an X-ray for a thick object such as piping.

Some scintillators have characteristics that change in response to irradiation with radiation, and such a phenomenon is also referred to as "burn-in (bright burn)".

Due to the phenomenon, an artifact or an afterimage of an object occurs in a radiographic image. However, there is a problem that it takes time to restore the radiographic image. Therefore, a correction method of eliminating burn-in is known.

Japanese Patent Laid-Open No. 2003-185752 describes a method of calculating a parameter and correcting an image using a current captured burn-in image, a previous burn-in image, and an image of burn-in information.

In the method disclosed in Japanese Patent Laid-Open No. 2003-185752, it is necessary to distinguish an image projected by image capturing and an image due to burn-in, and it is difficult to accurately correct the image due to the burn-in.

In view of the situation described above, it is desirable to provide a radiation imaging system that can reduce the burn-in itself.

SUMMARY

Aspects of the present disclosure provide a radiation imaging apparatus which includes a radiation detecting panel configured to convert radiation emitted from a radiation generating apparatus into an image signal, and a burn-in estimating unit configured to estimate, from the image signal, a probability that burn-in of the radiation detecting panel due to the radiation occurs. Based on the result of the estimation by the burn-in estimating unit, the radiation generating apparatus is stopped or a warning for stopping the radiation generating apparatus is output, and the image signal is displayed.

Further features of the present disclosure will become apparent from the following description of embodiments (with reference to the attached drawings).

BRIEF DESCRIPTION OF THE DRAWINGS

FIG. 4 is a diagram illustrating an example of an operation of the radiation imaging system according to the embodiment of the present disclosure.

DESCRIPTION OF THE EMBODIMENTS

Hereinafter, embodiments are described with reference to the accompanying drawings. The following embodiments do not limit the disclosure described in the claims. Although a plurality of features are described in the embodiments, not all the features are necessarily essential for the disclosure, and two or more of the plurality of features may be arbitrarily combined. In the accompanying drawings, the same or similar configurations are denoted by the same reference signs, and duplicate descriptions are omitted.

First Embodiment

Figure 1:
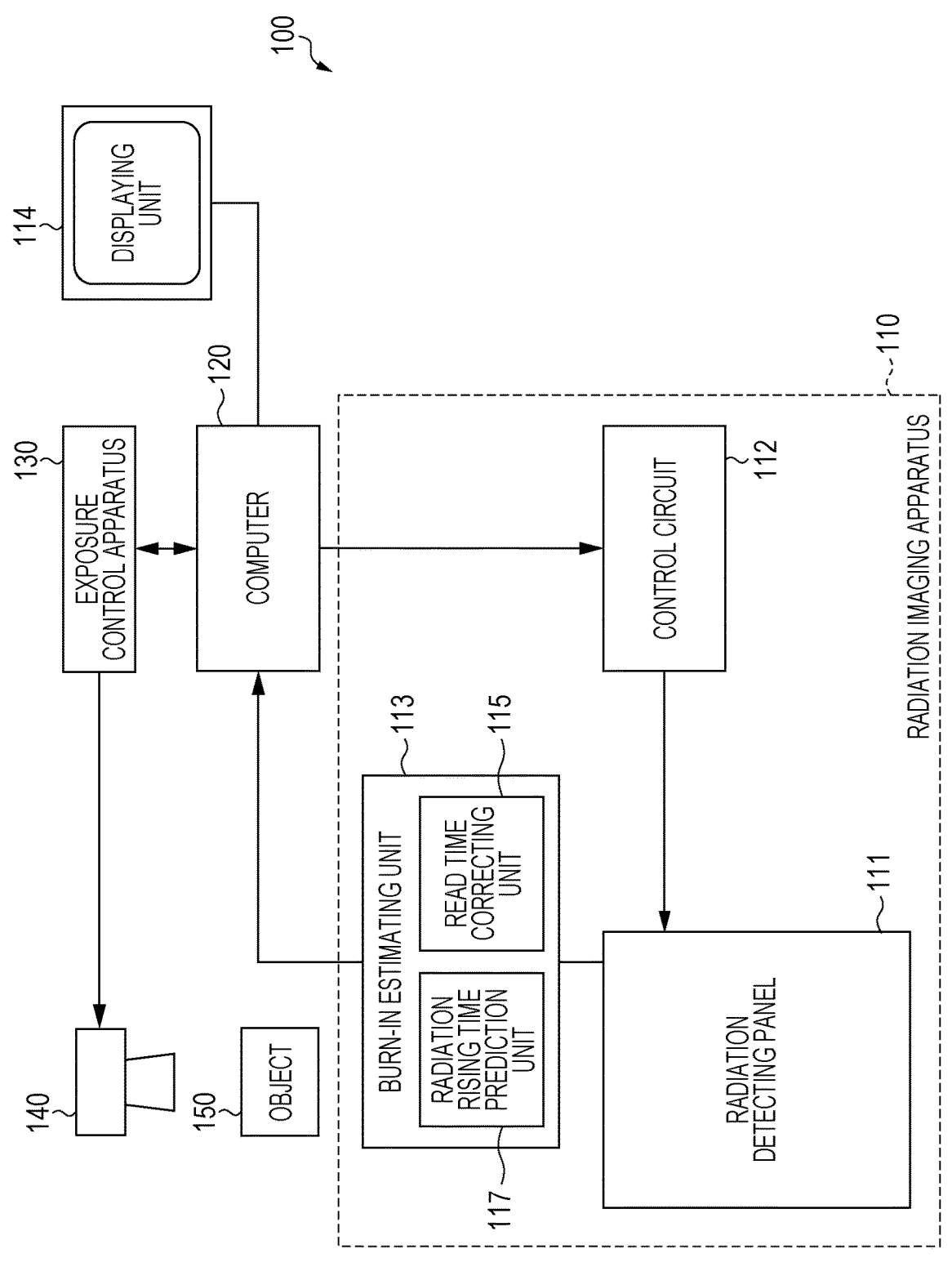
FIG. 1 is a diagram illustrating an example of a configuration of a radiation imaging system according to an embodiment of the present disclosure.

FIG. 1 illustrates a configuration of a radiation imaging system 100 according to a first embodiment of the present disclosure. The radiation imaging system 100 electrically captures an optical image formed by radiation to obtain an electric radiographic image. The radiation is typically an X-ray, but may be an α ray, a β ray, or a γ ray. The radiation imaging system 100 includes, for example, a radiation imaging apparatus 110, a computer 120, a displaying unit 114, an exposure control apparatus 130, and a radiation generating apparatus 140. Although described below in detail, the computer 120, the displaying unit 114, the exposure control apparatus 130, and the radiation generating apparatus 140 may be collectively referred to as external apparatuses with respect to the radiation imaging apparatus 110 in the following description.

The radiation generating apparatus 140 starts emitting radiation in accordance with an exposure instruction (instruction to emit radiation) from the exposure control apparatus 130. The radiation emitted by the radiation generating apparatus 140 is incident on the radiation imaging apparatus 110 through an object 150. The radiation generating apparatus 140 stops emitting radiation in accordance with a stop instruction from the exposure control apparatus 130.

The radiation imaging apparatus 110 includes a radiation detecting panel 111, a control circuit 112, and a burn-in estimating unit 113. The radiation detecting panel 111 generates an image signal according to the radiation incident on the radiation imaging apparatus 110 and transmits the generated image signal to the computer 120. Each of the exposure control apparatus 130, the radiation generating apparatus 140, and the computer 120 corresponds to an external apparatus that receives a radiation stop signal for stopping emission of radiation from the radiation imaging apparatus 110.

The image signal is data representing a radiographic image. The control circuit 112 controls an operation of the radiation detecting panel 111. For example, the control circuit 112 generates, based on the image signal received from the radiation detecting panel 111, a radiation stop signal (hereinafter also merely referred to as a stop signal) for stopping emission of radiation from the radiation generating apparatus 140. The stop signal is supplied to the exposure control apparatus 130. The exposure control apparatus 130 transmits a stop instruction to the radiation generating apparatus 140 in response to the stop signal. The control circuit 112 may include a programmable logic device (PLD) such as a field programmable gate array (FPGA), for example. Alternatively, the control circuit 112 may include a dedicated circuit such as an application specific integrated circuit (ASIC). Instead of this, the control circuit 112 may include a combination of a general-purpose processing circuit such as a processor and a storage circuit such as a memory. In this case, a function of the control circuit 112 may be implemented by the general-purpose processing circuit executing a program stored in the storage circuit.

In the field of non-destructive inspection of inspecting an internal flaw, a surface flaw, or deterioration of components such as a print board and piping without damaging the components, the exposure control apparatus 130 and the computer 120 may not be connected to each other for synchronization. In this case, a user directly operates the exposure control apparatus 130 to stop emission of radiation.

The burn-in estimating unit 113 determines whether there is a possibility that a scintillator may be burned in due to radiation emitted based on the image signal from the radiation detecting panel 111. The scintillator is a member that converts radiation into visible light. The scintillator may be hereinafter also referred to as a fluorescent member. In a case where there is a possibility that the scintillator may be burned in, the burn-in estimating unit 113 transmits a stop signal to the exposure control apparatus 130 and causes the exposure control apparatus 130 to stop the emission of radiation. In a case where the exposure control apparatus 130 and the computer 120 are not connected to each other for synchronization in the field of non-destructive inspection or the like, the burn-in estimating unit 113 causes the displaying unit 114 to display a warning for prompting the stop of emission of radiation and display an image representing a region in which there is a possibility that burn-in may occur.

The burn-in estimating unit 113 includes a radiation rising time predicting unit 117 and a read time correcting unit 115. The burn-in estimating unit 113 can accurately estimate burn-in of the scintillator.

The computer 120 includes a control unit that controls the radiation imaging apparatus 110 and the exposure control apparatus 130, a receiving unit that receives an image signal from the radiation imaging apparatus 110, and a signal processing unit that processes the image signal received from the radiation imaging apparatus 110. Each of the control unit, the receiving unit, and the signal processing unit may include a dedicated circuit or may include a combination of a general-purpose processing circuit and a storage circuit in a similar manner to the control circuit 112. As an example, the exposure control apparatus 130 includes an exposure switch. When the exposure switch is turned on by the user, the exposure control apparatus 130 transmits an exposure instruction to the radiation generating apparatus 140 and transmits, to the computer 120, a start notification indicating the start of emission of radiation. Upon receiving the start notification, the computer 120 notifies the control circuit 112 included in the radiation imaging apparatus 110 of the start of emission of radiation in response to the start notification.

In a case where the exposure control apparatus 130 and the computer 120 are not connected to each other for synchronization, the radiation detecting panel 111 continues an image read operation and detects the start of emission of radiation from an output value of the image signal.

Figure 2:
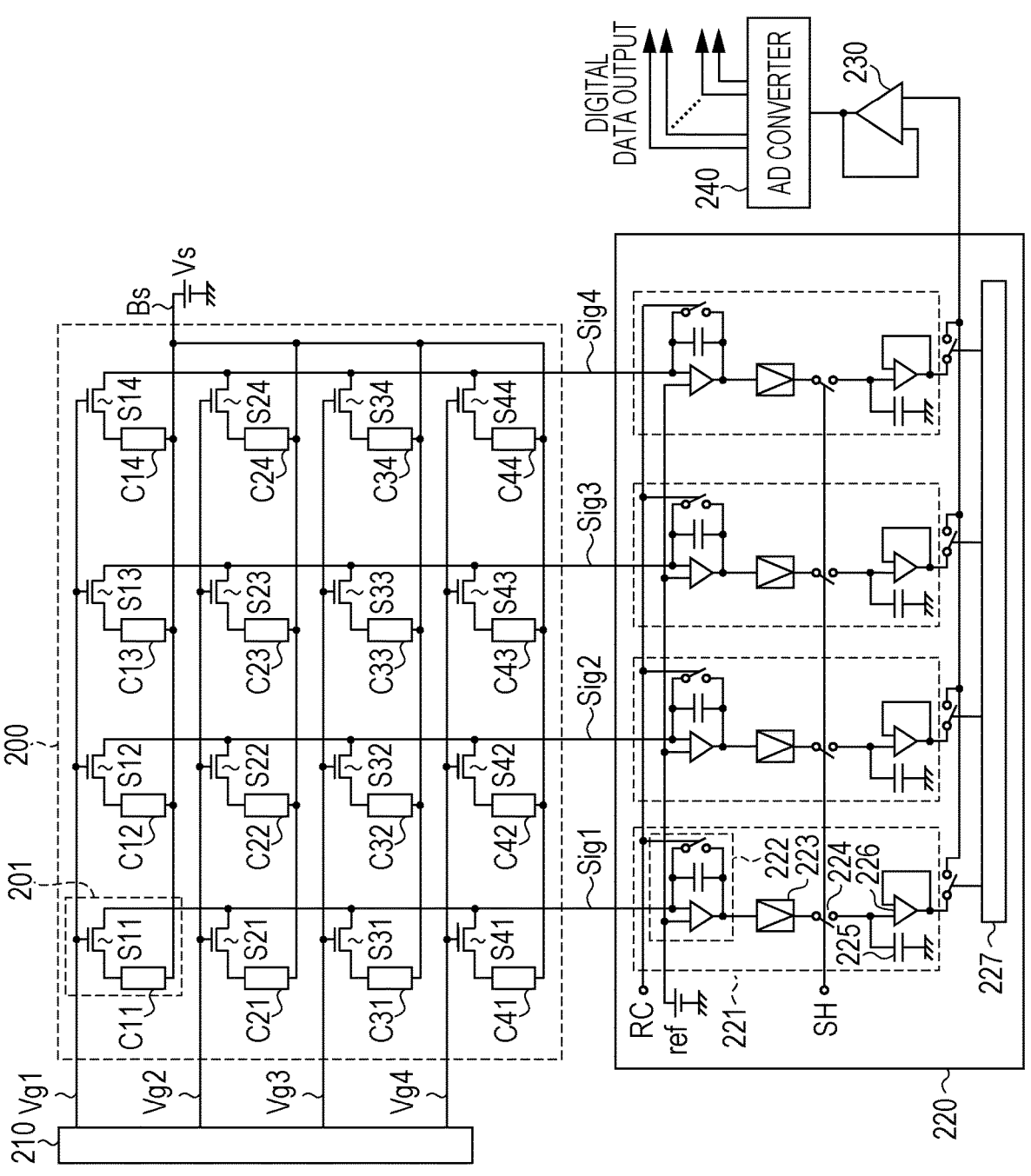
FIG. 2 is a diagram illustrating an example of a configuration of a radiation imaging apparatus according to the embodiment of the present disclosure.

FIG. 2 illustrates an example of a configuration of the radiation detecting panel 111. The radiation detecting panel 111 includes, for example, a pixel array 200, a drive circuit 210, a reading circuit 220, a buffer circuit 230, and an AD converter 240. The drive circuit 210 and the reading circuit 220 function as peripheral circuits of the pixel array 200. The pixel array 200 includes, for example, a plurality of pixels 201 arrayed in a matrix, a plurality of drive lines Vg1 to Vg4, a plurality of signal lines Sig1 to Sig4, and a bias line Bs. Hereinafter, the drive lines Vg1 to Vg4 may be merely referred to as drive lines, the signal lines Sig1 to Sig4 may be merely referred to as signal lines, and the bias line Bs may be merely referred to as a bias line. In FIG. 2, the pixel array 200 includes pixels 201 in four rows and four columns for description. However, the pixel array 201 may actually include a larger number of pixels 201. As an example, the radiation detecting panel 111 has dimensions of 17 inches and the pixel array 200 includes pixels 201 in approximately 3000 rows and approximately 3000 columns. Each of the pixels 201 includes a switch element and a conversion element that converts visible light emitted from the scintillator into an electric charge and generates a charge signal.

The pixel array 200 includes a plurality of conversion elements C11 to C44 and a plurality of switch elements S11 to S44. In the following description, the conversion elements C11 to C44 are collectively referred to as conversion elements C. Description regarding each of the conversion elements C applies to each of the conversion elements C11 to C44. Similarly, the switch elements S11 to S44 are collectively referred to as switch elements S, the drive lines Vg1 to Vg4 are collectively referred to as drive lines Vg, and the signal lines Sig1 to Sig4 are collectively referred to as signal lines Sig. The rows of the pixel array 200 are referred to as first to fourth rows from the top side of FIG. 2, and the columns of the pixel array 200 are referred to as first to fourth columns from the left side of FIG. 2. Each of the pixels 201 includes a combination of a single conversion element C and a single switch element S. For example, the pixel 201 in the first row and the second column includes a combination of the conversion element C12 and the switch element S12. A unit including a plurality of pixels may be referred to as a pixel unit, and the pixel unit may be referred to as a converting unit.

In each of the pixels 201, the conversion element C converts incident radiation into an electric signal (for example, an electric charge) and the switch element S is connected between the conversion element C and a signal line Sig corresponding to the conversion element C. For example, the switch elements S11, S21, S31, and S41 are connected between the signal line Sig1 and the plurality of
conversion elements C11, C21, C31, and C41. When the
switch element S is turned on, the conversion element C and
the signal line Sig become electrically conductive and the
electric signal (for example, an electric charge accumulated
in the conversion element C) obtained by the conversion
element C is transmitted to the signal line Sig. For example,
the conversion element C may be disposed above an insu-
lating substrate such as a glass substrate and may be an MIS
type photodiode containing amorphous silicon as a main
material. The conversion element C may be a PIN type
photodiode instead of the MIS type photodiode. The con-
version element C may be configured as a direct type
conversion element that directly converts radiation into an
electric charge. Alternatively, the conversion element C may
be configured as an indirect type conversion element that
converts radiation into light and detects the light after the
conversion. In a case where the conversion element C is of
the indirect type, the scintillator may be shared by the
plurality of pixels 201.

The switch element S may include a transistor, such as a
thin film transistor (TFT), having a control terminal (gate)
and two main terminals (source and drain). The conversion
element C includes two main electrodes. One of the main
electrodes of the conversion element C is connected to one
of the two main terminals of the switch element S, and the
other of the main electrodes of the conversion element C is
connected to a bias power source Vs via the common bias
line Bs. The bias power source Vs generates a bias voltage.

The control terminals of the switch elements S of the
pixels 201 in the first row are connected to the drive line
Vg1. The control terminals of the switch elements S of the
pixels 201 in the second row are connected to the drive line
Vg2. The same applies to the third and fourth rows. In this
manner, each of the drive lines is connected to the pixels 201
in a respective one of the rows in such a way that the pixels
201 can be controlled via the drive lines in units of the rows.
Each of the signal lines can transfer charge signals of the
pixels 201 in a respective one of the columns in units of the
columns.

The drive circuit 210 supplies a drive signal to the control
terminal of the switch element S of each of the pixels 201
through the drive lines Vg in accordance with a control
signal supplied from the control circuit 112. The control
signal includes an ON signal (high-level voltage in the
following description) for turning on the switch element S
and an OFF signal (low-level voltage in the following
description) for turning off the switch element S. The drive
circuit 210 includes, for example, a shift register. This shift
register performs a shift operation in accordance with a
control signal (for example, a clock signal) supplied from
the control circuit 112.

The reading circuit 220 amplifies and reads the electric
signals obtained by the conversion elements C and appear-
ing in the signal lines Sig. The reading circuit 220 includes
a single amplifying circuit 221 for each of the signal lines
Sig. In the example illustrated in FIG. 2, since the pixel array
200 includes the four signal lines Sig, the reading circuit 220
includes four amplifying circuits 221. Each of the amplify-
ing circuits 221, which are also referred to as column
amplifiers CA, includes, for example, an integral amplifier
222, a variable amplifier 223, a switch element 224, a
capacitance 225, and a buffer circuit 226. The switch ele-
ment 224 and the capacitance 225 forms a sample-and-hold
circuit. The integral amplifier 222 includes, for example, an
operation amplifier, and an integrating capacitance and a
reset switch that are connected in parallel between an inverting input terminal and an output terminal of the
operation amplifier. A reference voltage is supplied to a
non-inverting input terminal of the operation amplifier from
a reference power source Vref. When the reset switch is
turned on according to a control signal RC (reset pulse)
supplied from the control circuit 112, the integrating capaci-
tance is reset and the potential of the signal line Sig is reset
to a reference voltage.

The variable amplifier 223 amplifies a signal from the
integral amplifier 222 at a set amplification factor.

The sample-and-hold circuit samples and holds the signal
from the variable amplifier 223. A control signal SH sup-
plied from the control circuit 112 controls turning on and off
of the switch element 224 included in the sample-and-hold
circuit. The buffer circuit 226 performs buffering (imped-
ance conversion) on the signal from the sample-and-hold
circuit (impedance conversion) and outputs the signal.

The reading circuit 220 further includes a multiplexer 227
that selects and outputs signals from the plurality of ampli-
fying circuits 221 in predetermined order. The multiplexer
227 includes, for example, a shift register. This shift register
performs a shift operation in accordance with a control
signal (for example, the clock signal) supplied from the
control circuit 112. By the shift operation, one of the signals
from the plurality of amplifying circuits 221 is selected.

The buffer circuit 230 performs buffering (impedance
conversion) on a signal output from the multiplexer 227. The
AD converter 240 converts an analog signal output from the
buffer circuit 230 into a digital signal. The signal output
from the AD converter 240, that is, the image signal is
transmitted to the computer 120.

Figure 3:
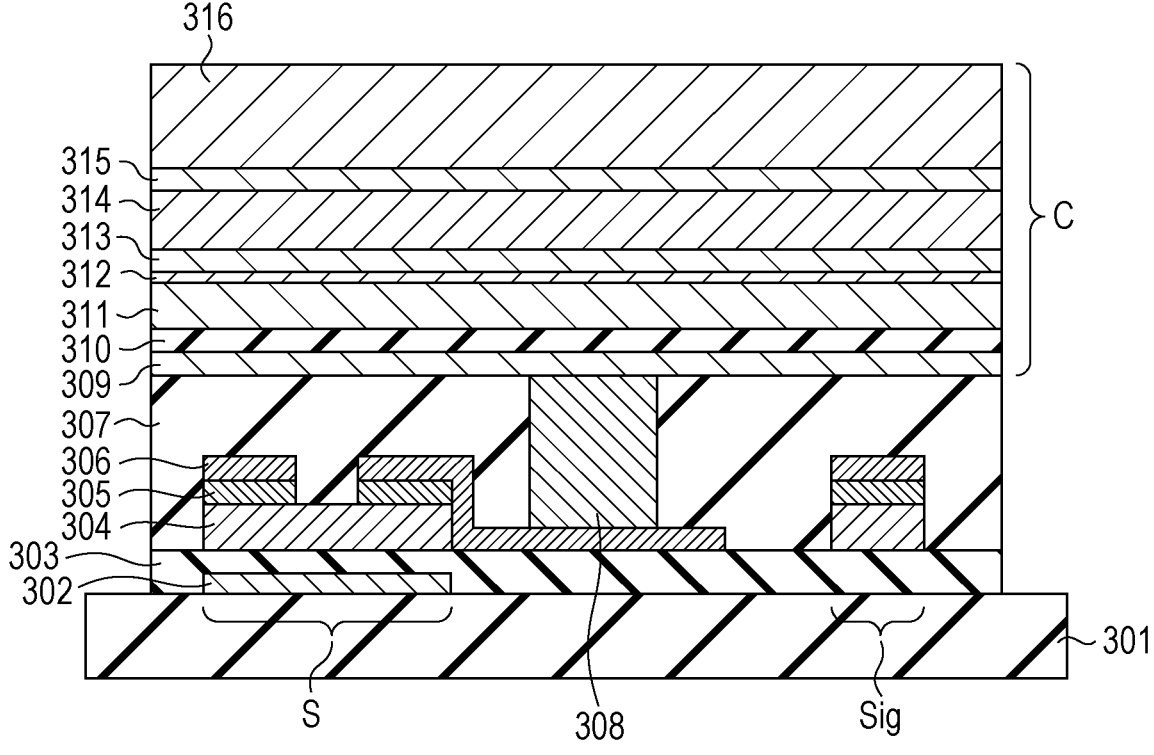
FIG. 3 is a diagram illustrating an example of a section structure of a pixel according to the embodiment of the present disclosure.
Figure 5:
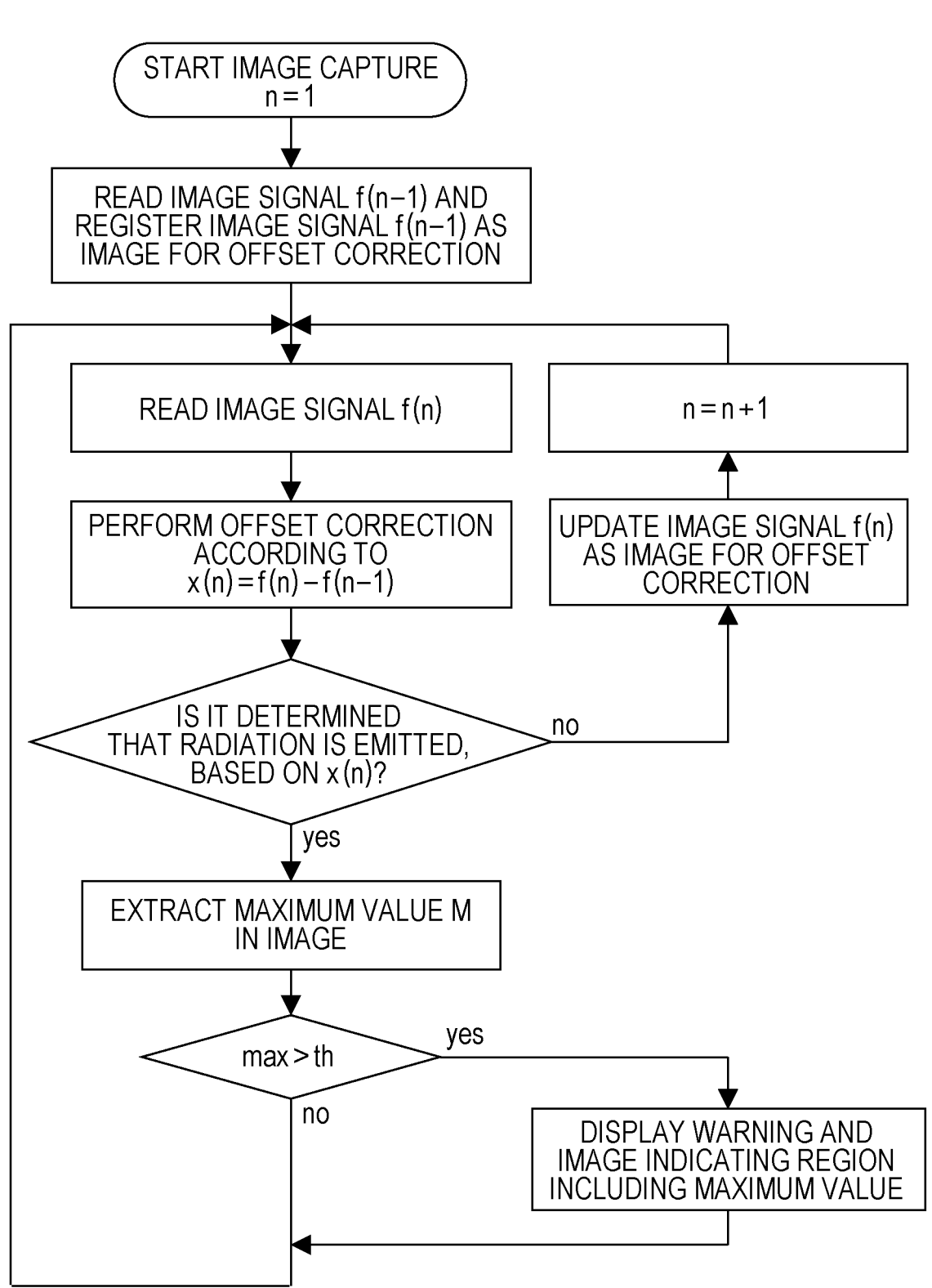
FIG. 5 is a diagram illustrating a procedure of an operation of the radiation imaging system according to the embodiment of the present disclosure.

FIG. 3 schematically illustrates an example of a section
structure of a single pixel 201 included in the pixel array
200. The pixel 201 is formed on the insulating substrate 301
such as a glass substrate. The pixel 201 includes an elec-
troconductive layer 302, an insulating layer 303, a semicon-
ductor layer 304, an impurity semiconductor layer 305, and
an electroconductive layer 306 on the insulating substrate
301. The electroconductive layer 302 forms the gate of the
transistor (for example, a TFT) forming the switch element
S. The insulating layer 303 is disposed to cover the elec-
troconductive layer 302. The semiconductor layer 304 is
disposed on a portion included in the electroconductive layer
302 and forming the gate via the insulating layer 303. The
impurity semiconductor layer 305 is disposed on the semi-
conductor layer 304 and forms the two main terminals
(source and drain) of the transistor forming the switch
element S. The electroconductive layer 306 forms a wiring
pattern connected to the two main terminals (source and
drain) of the transistor forming the switch element S. A
portion of the electroconductive layer 306 forms a portion of
the signal line Sig, and another portion of the electrocon-
ductive layer 306 forms a wiring pattern for connecting the
conversion element C to the switch element S.

The pixel 201 further includes an inter-layer insulating
film 307 covering the insulating layer 303 and the electro-
conductive layer 306.

In the inter-layer insulating film 307, a contact plug 308
for connection to the electroconductive layer 306 (switch
element S) is disposed. The pixel 201 further includes an
electroconductive layer 309, an insulating layer 310, a
semiconductor layer 311, an impurity semiconductor layer
312, an electroconductive layer 313, a protecting layer 314,
an adhesive layer 315, and a scintillator 316 on the inter-
layer insulating film 307 in this order. These layers 309 to
316 form the indirect type conversion element C. The
electroconductive layer 309 and the electroconductive layer 313 form a lower electrode and an upper electrode of a photoelectric conversion element forming the conversion element C, respectively. The electroconductive layer 313 is made of, for example, a transparent material. The electroconductive layer 309, the insulating layer 310, the semiconductor layer 311, the impurity semiconductor layer 312, and the electroconductive layer 313 form an MIS sensor as a photoelectric conversion element. The impurity semiconductor layer 312 is formed as, for example, an N-type impurity semiconductor layer. The scintillator 316 is made of, for example, a gadolinium-based material or a cesium iodide (CsI) material and converts radiation into light.

Instead of the example described above, the conversion element C may be a direct type conversion element that directly converts incident radiation into an electric signal (electric charge). An example of the direct type conversion element C is a conversion element containing amorphous selenium, gallium arsenide, gallium phosphorus, lead iodide, mercury iodide, CdTe, CdZnTe, or the like as a main material. The conversion element C is not limited to an MIS type conversion element and may be, for example, a PN-type photodiode or a PIN type photodiode.

In the example illustrated in FIG. 3, in an orthogonal projection (plan view) to a surface on which the pixel array 200 is formed, each of the signal lines Sig overlaps parts of the conversion elements C. This configuration has an advantage that the area of the conversion element C of each of the pixels 201 can be large, but has a disadvantage that capacitive coupling between the signal lines Sig and the conversion elements C is large. When radiation is incident on the conversion element C, an electric charge is accumulated in the conversion element C, and the potential of the electroconductive layer 309 (lower electrode) changes, the potential of the signal line Sig also changes due to capacitive coupling between the signal line Sig and the conversion element C.

An example of an operation of the radiation imaging system 100 is described with reference to FIG. 4. The operation of the radiation imaging system 100 is controlled by the computer 120. An operation of the radiation imaging apparatus 110 is controlled by the control circuit 112 under control by the computer 120. For example, the operation illustrated in FIG. 4 is started when the user of the radiation imaging system 100 gives an instruction to the radiation imaging system 100.

Figure 4:
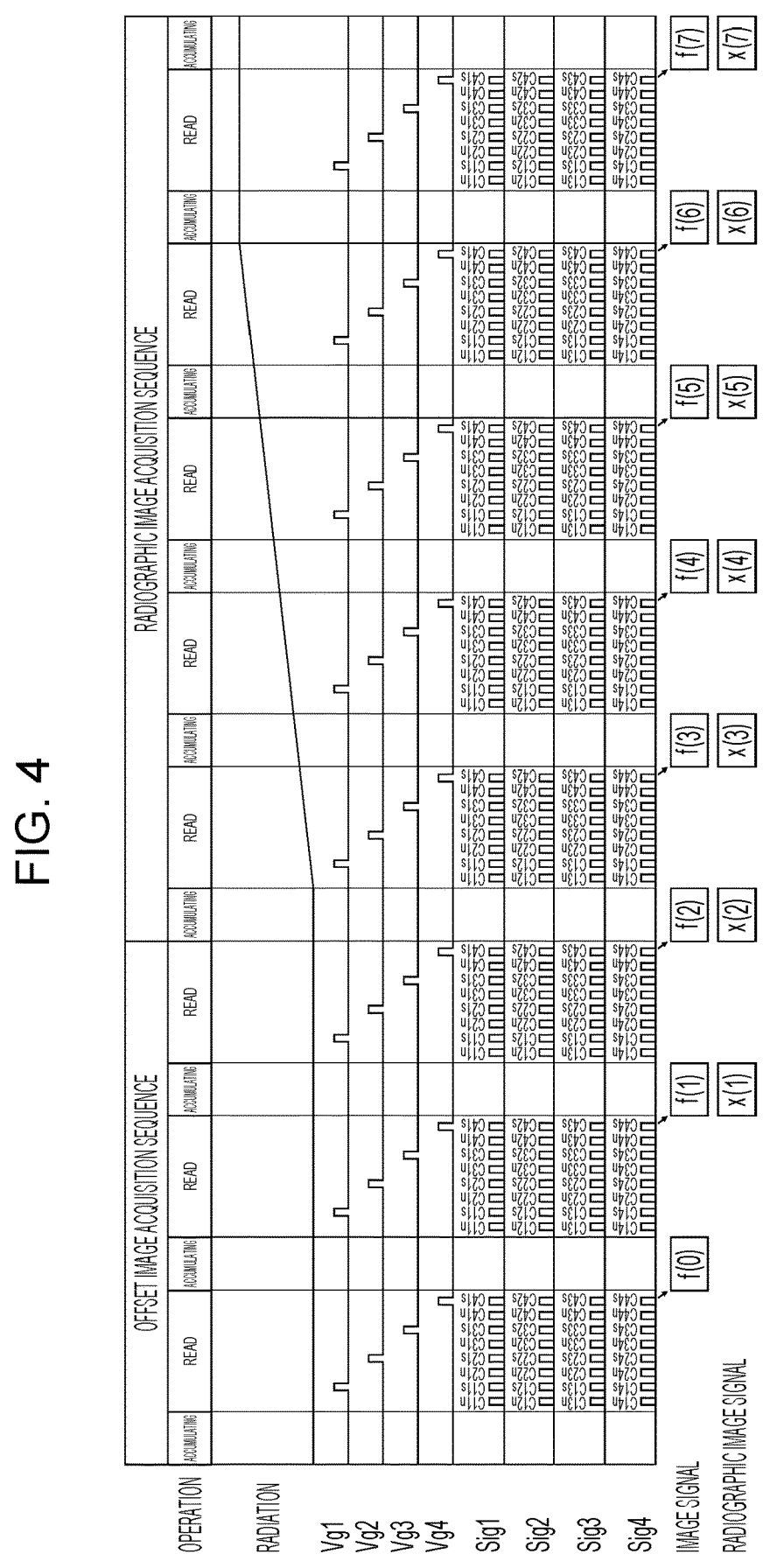

"Operation" illustrated in FIG. 4 represents the operation of the radiation imaging system 100. The operation of the radiation imaging system 100 includes an offset image acquisition sequence and a radiographic image acquisition sequence. The offset image acquisition sequence is a series of operations that are performed while the radiation imaging system 100 waits for the start of emission of radiation. The offset image acquisition sequence is the series of operations for acquiring an offset image. The radiographic image acquisition sequence is a series of operations for acquiring a radiographic image. The offset image is an image formed by signals obtained from the pixels 201 in a state in which the radiation imaging apparatus 110 is not irradiated with radiation. "Radiation" illustrated in FIG. 4 represents whether the radiation imaging apparatus 110 is irradiated with radiation. A low level indicates that the radiation imaging apparatus 110 is not irradiated with radiation, while a high level indicates that the radiation imaging apparatus 110 is irradiated with radiation. "Vg1" to "Vg4" illustrated in FIG. 4 represent levels of drive signals supplied from the drive circuit 210 to the drive lines Vg1 to Vg4, respectively. The switch elements S connected to the drive line Vg to which a low-level drive signal (OFF signal) is supplied are OFF. The switch elements S connected to the drive line Vg to which a high-level drive signal (ON signal) is supplied are ON. "Sig1" to "Sig4" illustrated in FIG. 4 represent whether signals are read through the signal lines Sig1 to Sig4, respectively, and represent conversion elements C to be read. When each of "Sig1" to "Sig4" is at a low level", each of "Sig1" to "Sig4" represents that a signal is not read. When each of "Sig1" to Sig4" is at a high level", each of "Sig1" to "Sig4" represents that a signal is read. When each of "Sig1" to Sig4" is at a high level", each of "Sig1" to Sig4" represents a sign of a conversion element C to be read.

The offset image acquisition sequence includes an accumulating operation and a read operation. In the accumulating operation, the drive circuit 210 supplies an offset signal to each of the drive lines Vg1 to Vg4 for a predetermined time period. Therefore, an electric charge corresponding to radiation incident on each of the conversion elements C is accumulated in each of the conversion elements C. Subsequently, in the read operation, the control circuit 112 reads the electric charge (electric signal) accumulated in each of the conversion elements C.

The read operation is described below in detail. Although an electric charge read through the signal line Sig1 is mainly described below, the same applies to electric charges read through the signal lines Sig2 to Sig4.

First, the drive circuit 210 supplies an OFF signal to the drive lines Vg1 to Vg4. The switch elements S11 to S44 are turned off by the supply of the OFF signal, a leak current and a noise component of the switch elements appear in the signal line Sig1, and a charge signal C11$n$ at a reference level is read.

Next, the drive circuit 210 supplies an ON signal only to the drive line Vg1. By the supply of the ON signal, the switch element S11 is turned on and the conversion element C11 and the signal line Sig1 become electrically conductive. Therefore, a charge signal C11$s$ obtained by the conversion element C11 is read into the signal line Sig1.

Next, the drive circuit 210 supplies an OFF signal to the drive lines Vg1 to Vg4 again. The switch elements S11 to S44 are turned off by the supply of the OFF signal, a leak current and a noise component of the switch elements appear in the signal line Sig1, and a charge signal C21$n$ at the reference level is read.

Next, the drive circuit 210 supplies an ON signal only to the drive line Vg2. By the supply of the ON signal, the switch element S21 is turned on and the conversion element C21 and the signal line Sig1 become electrically conductive. Therefore, a charge signal C21$s$ obtained by the conversion element C21 is read into the signal Sig1.

By repeating this operation from the drive line Vg1 through the drive lines Vg2 and Vg3 to the drive line Vg4, charge signals C11$n$ to C44$n$ at the reference level and pixel signals C11$s$ to C44$s$ read from the conversion elements are output.

The charge signals C11$n$ to C44$n$ at the reference level obtained by the offset image acquisition sequence and the pixel signals C11$s$ to C44$s$ read from the conversion elements are transmitted to the multiplexer 227. An image signal obtained from the charge signals C11$n$ to C44$n$ and the pixel signals C11$s$ to C44$s$ is output from the multiplexer 227 through the buffer circuit 230 to the AD converter 240 and converted into a digital signal by the AD converter 240. The charge signals C11$n$ to C44$n$ at the reference level and the pixel signals C11$s$ to C44$s$ read from the conversion elements are subjected to differential processing of calculating "C11$s$–C11$n$" to "C44$s$–C44$n$". Thereafter, a single image signal f(0) is generated by synthesizing signals obtained by the differential processing. Although the differential processing is performed to calculate differences between the pixel signals C11$s$ to C44$s$ and the charge signals C11$n$ to C44$n$ at the reference level in order to remove noise components of the pixel signals C11$s$ to C44$s$, it is not necessary to perform the differential processing in a case where noise components of the pixel signals C11$s$ to C44$s$ are small.

The radiographic image acquisition sequence is different from the offset image acquisition sequence in that radiation is emitted from the radiation generating apparatus 140 in the radiographic image acquisition sequence. The radiographic image acquisition sequence is identical in operation to the offset image acquisition sequence.

Next, a procedure of an operation of the radiation imaging system 100 is described with reference to FIGS. 1, 4, 5, and 6. First, the procedure is described with reference to a flowchart of FIG. 5.

When image capturing is started, the image signal f(0) is read and registered as an image for offset correction. Subsequently, an image signal f(1) is acquired. Thereafter, offset correction processing (differential processing) of calculating the image signal f(1)—the image signal f(0) is performed to generate a radiographic image signal x(1). Next, it is determined whether radiation is emitted, based on an output value of the radiographic image signal x(1). When the output value is low and radiation is not emitted, the image signal f(1) is updated as an image for offset correction.

In this case, a single image signal is used as an image for offset correction, but a plurality of image signals may be averaged to reduce a noise component. Subsequently, an image signal f(2) is read. The same process as described above is repeatedly performed until the emission of radiation is started.

In the example illustrated in FIG. 4, the radiation generating apparatus 140 starts emitting radiation at a time point at which a radiographic image signal x(3) is generated. Next, the burn-in estimating unit 113 extracts a maximum value M in an image from the radiographic image signal x(3) after the offset correction and compares the maximum value M with a burn-in determination threshold th. It is possible to extract the accurate maximum value M by calculating an average value of the plurality of pixels or by applying filter processing on the radiographic image signal x(3) using a median filter or the like.

Figure 6:
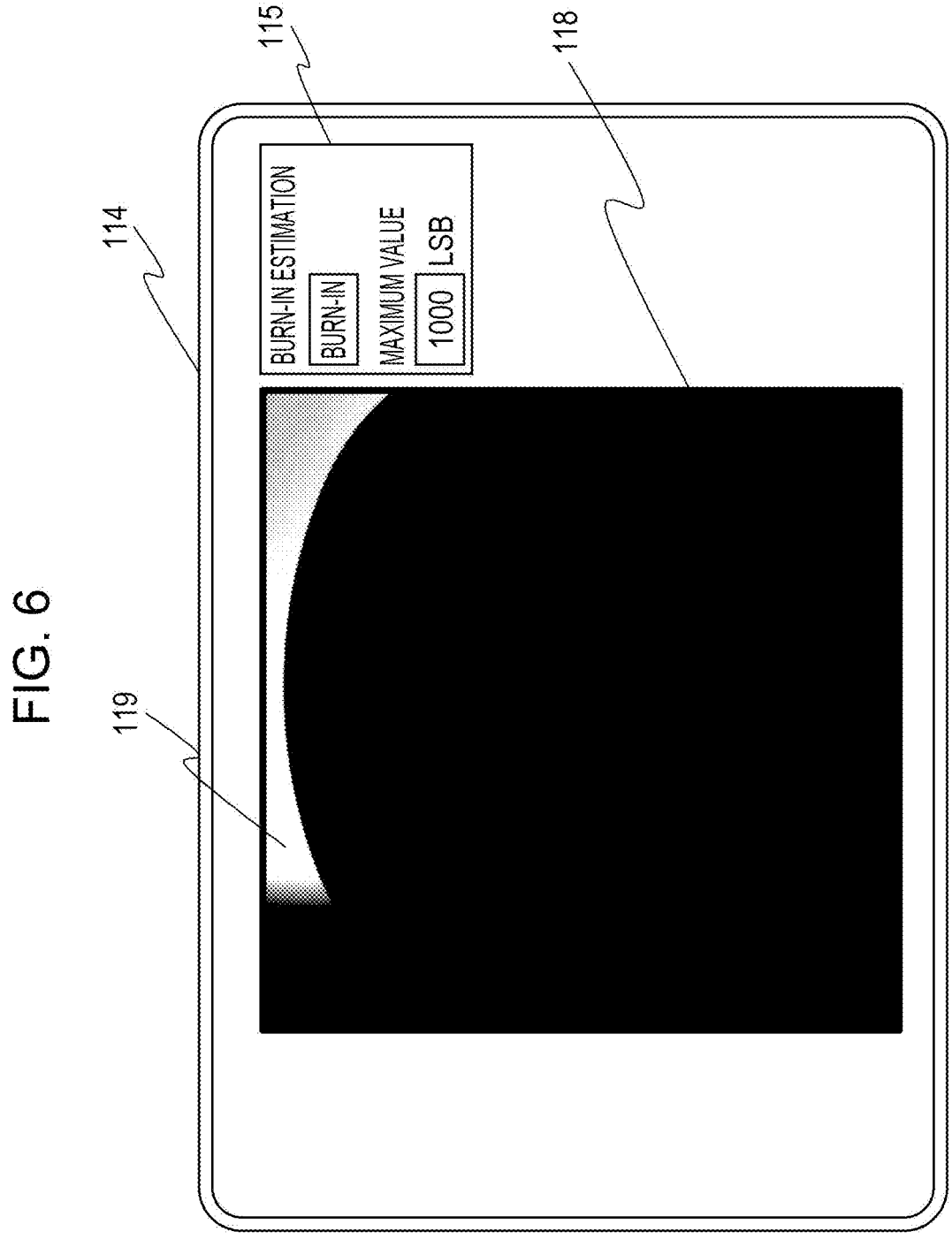
FIG. 6 is a diagram illustrating an example of a display of the radiation imaging system according to the embodiment of the present disclosure.

In a case where the maximum value M in the image exceeds the burn-in determination threshold th, the burn-in estimating unit 113 transmits a warning signal for prompting the stop of the emission of radiation to the displaying unit 114 in order to cause the displaying unit 114 to display information indicating that there is a possibility that burn-in may occur. FIG. 6 illustrates the acquired radiographic image signal x(3) and the result of the comparison by the burn-in estimating unit 113 that are displayed by the displaying unit 114. When a burn-in warning is output, the user can prevent burn-in by viewing the radiographic image signal displayed by the displaying unit 114 and taking measures to narrow down regions irradiated with radiation or the like. In addition, it is possible to prevent burn-in by disposing a shielding material between the radiation imaging apparatus 110 and the radiation generating apparatus 140, changing a layout of the object, or taking other measures.

In a case where only a region in which the maximum value exceeds the burn-in determination threshold th is displayed in a different color in an image displayed by the displaying unit 114, an abnormal portion is clearly visible.

For example, the radiographic image signal is normally displayed in grayscale, but only a region in which the maximum value exceeds the burn-in determination threshold th may be displayed in color.

Regions in an image displayed by the display unit 114 may be binarized and displayed. For example, a region in which the maximum value exceeds the burn-in determination threshold th may be displayed in white, and a region in which the maximum value is equal to or lower than the burn-in determination threshold th may be displayed in black. When a warning is displayed, the user can prevent burn-in by immediately stopping the emission of radiation from the radiation generating apparatus 140.

In the present embodiment, since the exposure control apparatus 130 and the computer 120 are not connected to each other for synchronization, a warning is displayed by the displaying unit 114. However, in a case where the exposure control apparatus 130 and the computer 120 are connected to each other and synchronized with each other, the computer 120 may transmit a stop signal to the exposure control apparatus 130 and cause the exposure control apparatus 130 to stop the emission of radiation from the radiation generating apparatus 140. In a case where the exposure control apparatus 130 and the computer 120 are not connected to each other for synchronization, a next image signal f(4) is subsequentially read. After offset correction, the burn-in estimating unit 113 extracts the maximum value M of the radiographic image signal x(3) and compares the extracted maximum value M with the burn-in determination threshold th. In a case where the maximum value M exceeds the burn-in determination threshold th, the displaying unit 114 displays information indicating that there is a possibility that burn-in may occur. The burn-in determination is repeated while the emission of radiation is continued. In a case where there is a possibility that burn-in may occur, the radiographic image signal is monitored to enable the emission of radiation to be immediately stopped.

In a case where a radiation generating apparatus that generates radiation using a high voltage of 150 kV to 300 kV is used in a non-destructive inspection apparatus, it takes several seconds for radiation to rise in order to increase a tube voltage. For example, in a case where it takes 10 seconds for radiation to rise, and a single radiographic image signal is acquired per second, an output difference of approximately 10 times occurs between the first radiographic image signal and a radiographic image signal after 10 seconds after determination as to whether radiation is emitted is performed. Therefore, the radiation rising time predicting unit 117 can predict, from the maximum value M of the first radiographic image signal, the maximum value M of the radiographic image signal after 10 seconds. Specifically, the maximum value of the first radiographic image is corrected based on the prediction result, and the maximum value of the image signal after 10 seconds is predicted in advance. Therefore, it is possible to estimate burn-in before irradiation with the maximum dose is performed 10 seconds after the start of emission of radiation. Burn-in of the scintillator depends on the dose of radiation emitted. Therefore, since burn-in can be determined at a stage where the dose is small, it is possible to reduce burn-in.

Burn-in is estimated from a radiographic image signal. Burn-in is a phenomenon in which a pattern of an object appears in an image. Burn-in occurs due to a direct incidence portion where an object does not appear and the radiation imaging apparatus 110 is irradiated with a large amount of radiation, and an object portion 118 where the radiation imaging apparatus 110 is irradiated with a small amount of radiation due to absorbance of radiation by the object. Therefore, the maximum value within the radiographic image signal may be treated as the direct incidence portion 119, the minimum value within the radiographic image signal may be treated as the object portion 118, and burn-in may be determined based on the ratio of the direct incidence portion to the object portion.

The calculation of the ratio of the direct incidence portion 119 to the object portion 118 is processing similar to the calculation of the transmittance of the object. Therefore, the threshold can be set based on the transmittance of the object. For example, in a case where the transmittance of the object is 5%, the ratio of the direct incidence portion to the object portion is 1/0.05=20. Therefore, in a case where the burn-in determination threshold th is set to 15 that is close to 20, and the ratio of the maximum value to the minimum value within the radiographic image signal exceeds 15, it is possible to determine that a direct incidence portion is present within the radiographic image signal and that there is a high possibility that burn-in may occur.

Even in a case where the determination is performed using the maximum value M of the radiographic image signal, and output is high in the entire radiographic image signal, it may be determined that there is a possibility that burn-in may occur. Meanwhile, in a case where the determination is performed using the ratio of the maximum value to the minimum value in the radiographic image signal, it is possible to distinguish the direct incidence portion 119 and the object portion 118 and accurately estimate burn-in.

Figure 7:
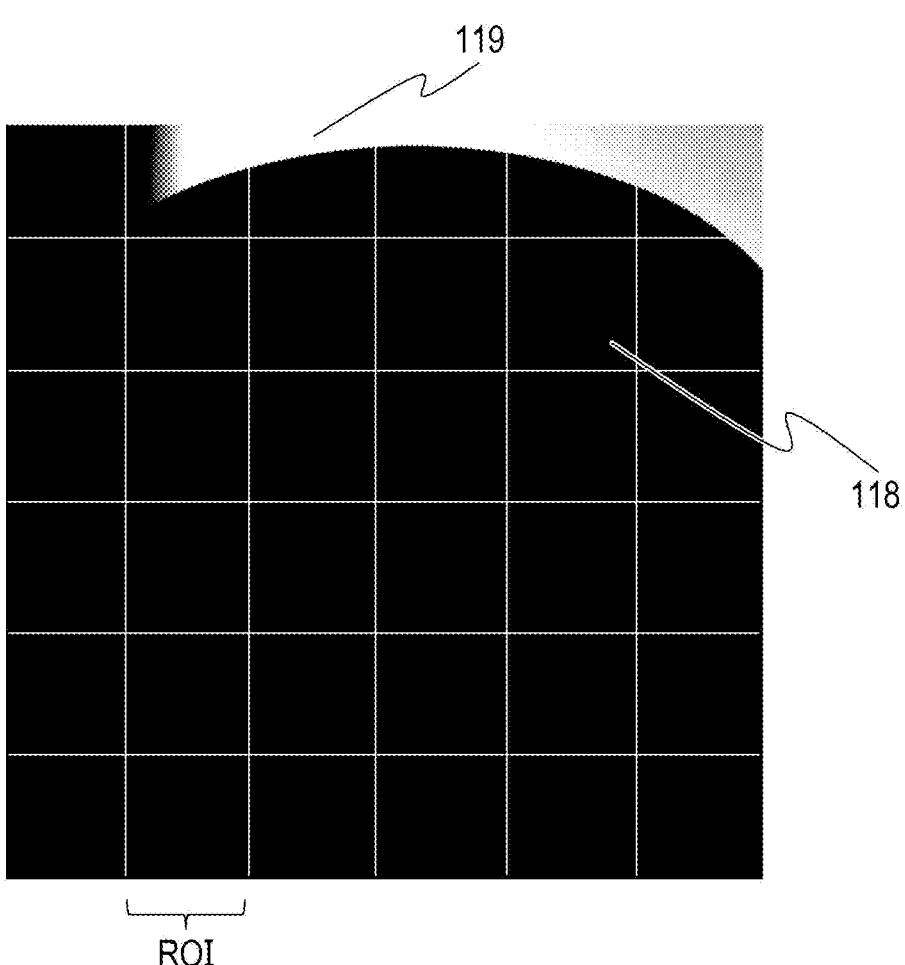
FIG. 7 is a diagram illustrating an example of a calculation region of the radiation imaging system according to the embodiment of the present disclosure.

Visually recognized burn-in often occurs at a boundary between the direct incidence portion 119 and the object portion 118. Therefore, as illustrated in FIG. 7, the radiographic image signal may be divided into a plurality of regions, the ratio of the maximum value to the minimum value in the divided regions of interest (ROIs) may be calculated, and the calculated ratio may be compared with the burn-in determination threshold th. In this case, in a case where shading occurs in the radiographic image signal, it is possible to eliminate an effect of the shading and accurately determine burn-in. In addition, a differential value (difference between adjacent pixels) within the radiographic image signal may be calculated. In this case, it is possible to more reliably eliminate the effect of the shading, as compared with the case where the radiographic image signal is divided into the plurality of regions and the calculation is performed.

Figure 8:
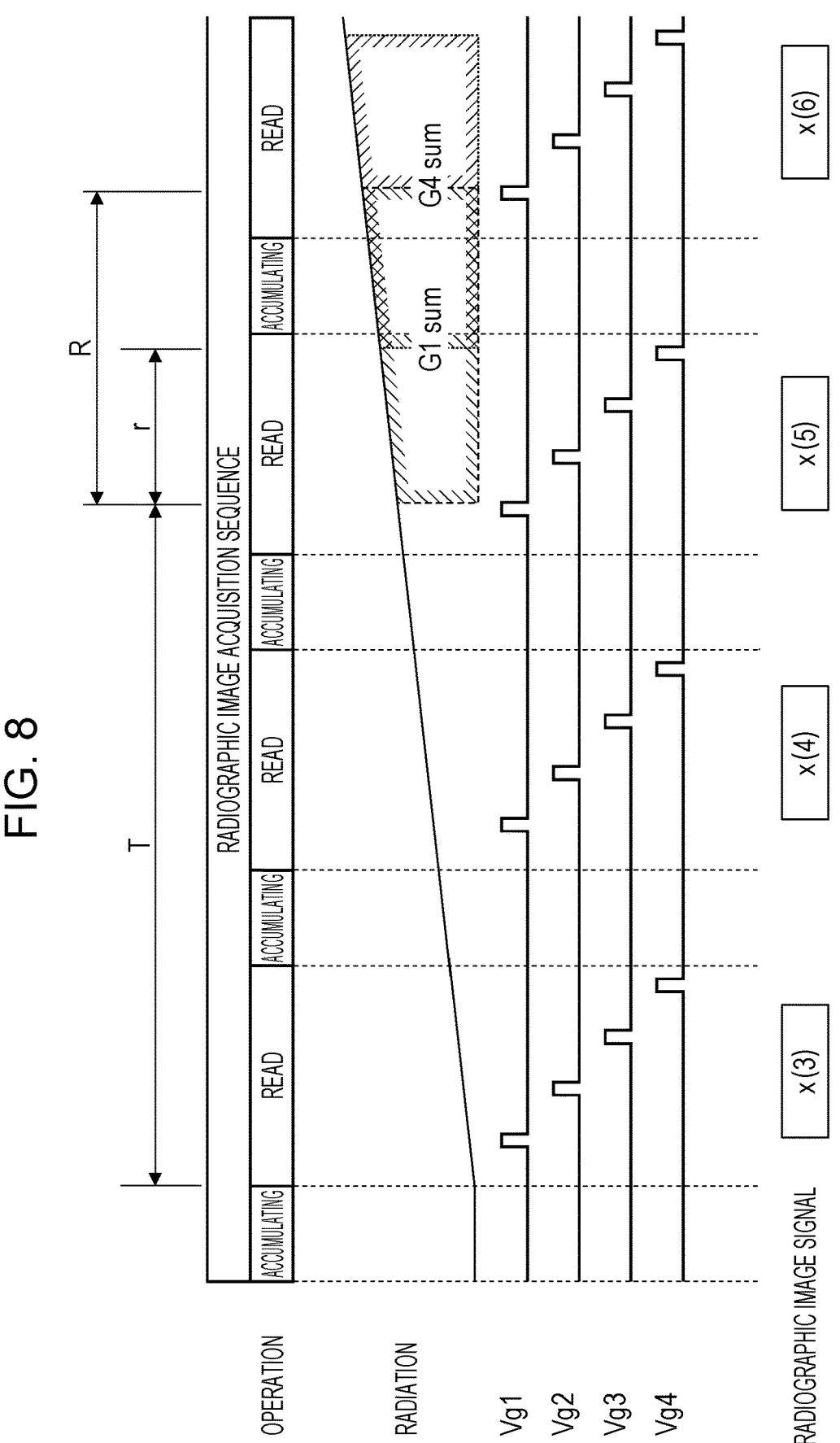
FIG. 8 is a diagram illustrating a calculation method of the radiation imaging system according to the embodiment of the present disclosure.

Next, the read time correcting unit 115 is described below with reference to FIG. 8. In the radiation generating apparatus 140 for non-destructive inspection, it takes time for radiation to rise. In addition, the radiation imaging apparatus 110 sequentially read signals row by row, the time when the radiation imaging apparatus 110 reads signals from the first row is different from the time when the radiation imaging apparatus 110 reads signals from the last row. Therefore, in a case where the radiation imaging apparatus 110 reads an image during the rising of the radiation, output from the first row is different from output from the last row.

A signal amount read through the drive line Vg1 in the first row for a radiographic image signal x(6) is described below. This signal amount is an integral value G1sum of dosage of radiation emitted from the time when the drive line Vg1 for a radiographic image signal x(5) of a previous frame is turned off to the time when the drive line Vg1 in the first row for the radiographic image signal x(6) is turned off. Next, a signal amount read through the drive line Vg4 in the last row for the radiographic image signal x(6) is described. This signal amount is an integral value G4sum of dosage of radiation emitted from the time when the drive line Vg4 for the radiographic image signal x(5) of the previous frame is turned off to the time when the drive line Vg4 in the last row for the radiographic image signal x(6) is turned off. Therefore, since the dosage of radiation from the radiation generating apparatus 140 gradually increases, the signal amount indicated by the integral value G4sum becomes larger than the signal amount indicated by the integral value G1sum.

The ratio of the integral value G4sum to the integral value G1sum is calculated according to the following equation, where T is a time from the start of emission of radiation, R is a time required for reading a single frame, and r is a difference between a time when signals are read from the first row and a time when signals are read from the last row.

$$G4sum/G1sum=(2(T+r)+R)/(2T+R)$$

Figure 9:
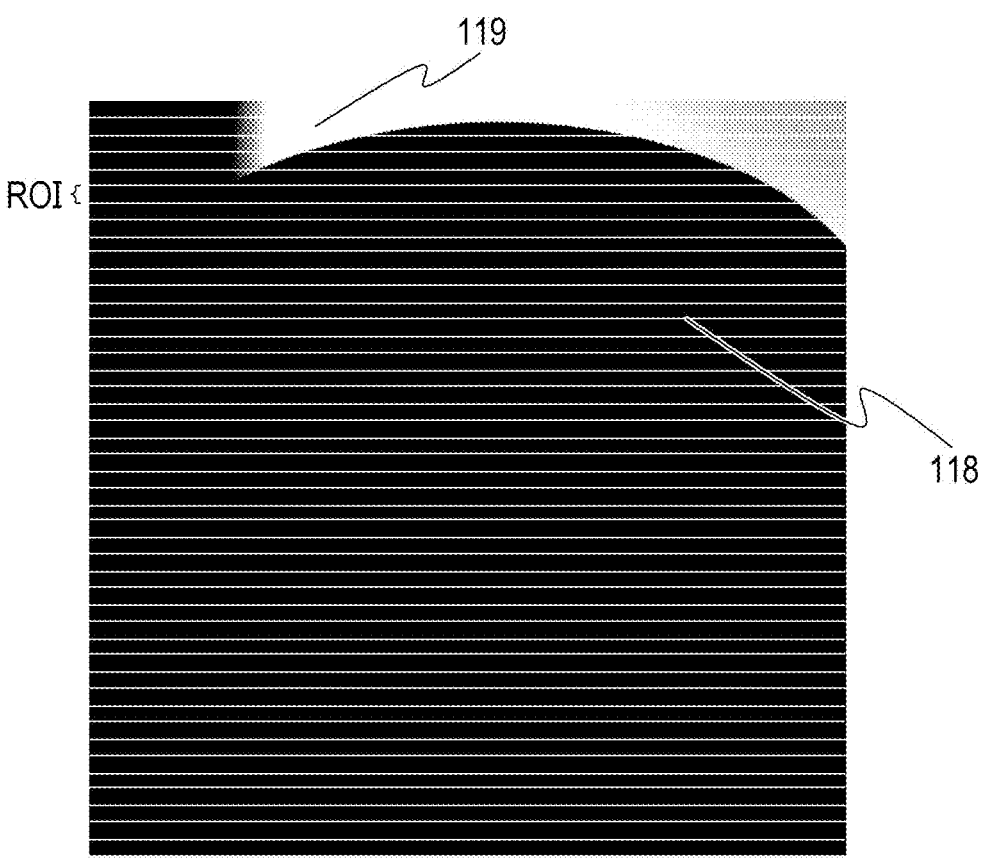
FIG. 9 is a diagram illustrating another example of the calculation region of the radiation imaging system according to the embodiment of the present disclosure.

Therefore, it is possible to correct output from the first to last rows by measuring a time from the start of emission of radiation, and uniformly determine burn-in in an image of a radiographic image signal. In addition, as illustrated in FIG. 9, in a case where the radiographic image signal is divided into a plurality of regions, the ratio of the maximum value to the minimum value in the regions of interest (ROIs) divided in the row direction may be calculated to eliminate an effect of a read time. According to this method, it is not necessary to measure a time from the start of emission of radiation.

Figure 10:
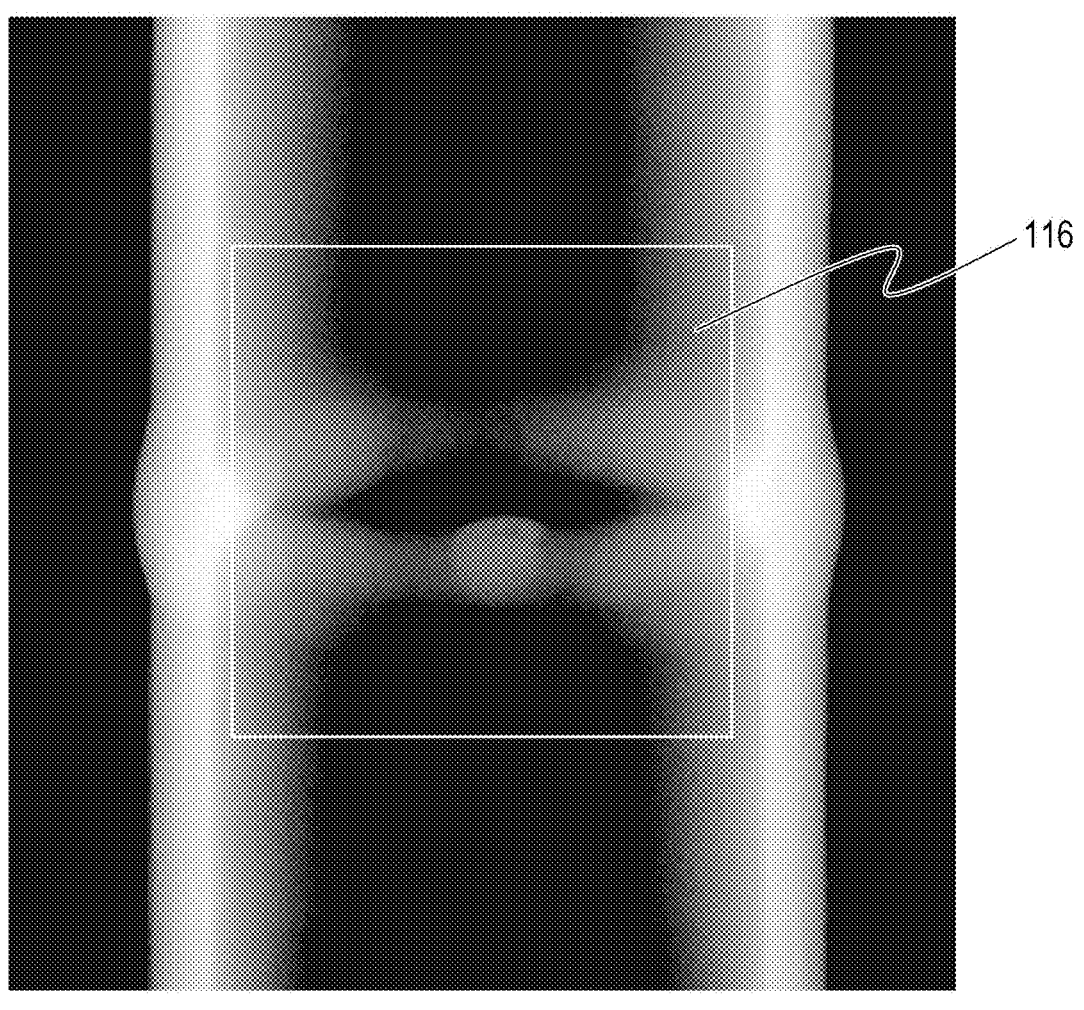
FIG. 10 is a diagram illustrating another calculation region of the radiation imaging system according to embodiment of the present disclosure.

As illustrated in FIG. 10, a range of a radiographic image signal to be used to estimate whether burn-in occurs may be set as a burn-in estimation region 116. In actual image capturing, a region of interest is present at the center of the radiographic image signal, and a peripheral portion of the radiographic image signal is present outside the region of interest. Therefore, even when burn-in occurs, the burn-in is unlikely to be a problem. For this region, it is important to determine whether burn-in does not occur in the region of interest. By setting the burn-in estimation region 116, it is possible to eliminate unnecessary burn-in estimation and it is possible to notify the user only of a warning necessary for the user.

The present disclosure is not limited to the above-described embodiments, and various changes and modifications can be made without departing from the spirit and scope of the present disclosure.

With the above-described units, it is possible to provide the system in which burn-in of the scintillator is reduced.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to embodiments, it is to be understood that the disclosure is not limited to the disclosed embodiments. The scope of the following claims is to be accorded the broadest interpretation so as to encompass all such modifications and equivalent structures and functions.

This application claims the benefit of priority from Japanese Patent Application No. 2022-186150, filed Nov. 22, 2022, which is hereby incorporated by reference herein in its entirety.

What is claimed is:

1. A radiation imaging apparatus comprising:

a radiation detecting panel configured to convert radiation into an image signal;

at least one memory storing a program; and at least one processor that, upon an execution of the stored program, is configured to operate as:

a burn-in estimating unit configured to estimate, from the image signal, a burn-in of the radiation detecting panel due to the radiation, wherein when the burn-in estimating unit estimates that the burn-in occurs, the burn-in estimating unit outputs information regarding a stop of an emission of the radiation to an external apparatus.

2. The radiation imaging apparatus according to claim 1, wherein the information regarding the stop of the emission of the radiation to the external apparatus is a warning signal for prompting to stop the emission of the radiation.

3. The radiation imaging apparatus according to claim 2, wherein the external apparatus is a display apparatus that receives the warning signal for prompting to stop the emission of the radiation and displays a warning.

4. The radiation imaging apparatus according to claim 1, wherein the information regarding the stop of the emission of the radiation to the external apparatus is a radiation stop signal for stopping the emission of the radiation.

5. The radiation imaging apparatus according to claim 1, wherein the burn-in estimating unit estimates the burn-in by comparing a maximum value of the image signal with a minimum value of the image signal.

6. The radiation imaging apparatus according to claim 1, the burn-in estimating unit estimates the burn-in by comparing a ratio of a maximum value of the image signal to a minimum value of the image signal with a threshold.

7. The radiation imaging apparatus according to claim 1, wherein the radiation detecting panel includes:

a scintillator configured to convert radiation into visible light, a converting unit including a plurality of pixels arrayed in a matrix, each of the plurality of pixels having a conversion element configured to convert the visible light into an electric charge and generate a charge signal, and a switch element configured to output the charge signal, a drive line for controlling switch elements in units of rows, a drive circuit configured to output an ON signal and an OFF signal to the drive line, a signal line configured to transfer charge signals in units of columns, and a reading circuit configured to amplify the charge signals transferred through the signal line and output the amplified charge signals as an image signal, wherein the burn-in estimating unit includes a correcting unit configured to correct the image signal based on a time when the image signal is read, and estimates the burn-in of the radiation detecting panel based on the image signal corrected by the correcting unit.

8. The radiation imaging apparatus according to claim 1, wherein the burn-in estimating unit estimates the burn-in of the radiation detecting panel based on the image signal in a set region.

9. A radiation imaging system comprising:

the radiation imaging apparatus according to claim 1; and the external apparatus.

10. A radiation imaging system comprising:

the radiation imaging apparatus according to claim 3; and the display apparatus.

* * * * *